(12) United States Patent
Kamrat

(10) Patent No.: US 9,766,176 B2
(45) Date of Patent: Sep. 19, 2017

(54) METHOD AND ARRANGEMENT IN CONNECTION WITH SEPARATE SAMPLE TAKEN FROM PROCESS LIQUID

(71) Applicant: JANESKO OY, Vantaa (FI)

(72) Inventor: Esko Kamrat, Vantaa (FI)

(73) Assignee: JANESKO OY, Vantaa (FI)

( * ) Notice: Subject to any disclaimer, the term of this patent is extended or adjusted under 35 U.S.C. 154(b) by 22 days.

(21) Appl. No.: 14/735,692

(22) Filed: Jun. 10, 2015

(65) Prior Publication Data

US 2015/0362429 A1    Dec. 17, 2015

(30) Foreign Application Priority Data

Jun. 11, 2014    (FI) ...................................... 20145539

(51) Int. Cl.
  *G01N 21/15*    (2006.01)
  *G01N 21/03*    (2006.01)

(52) U.S. Cl.
  CPC .......... *G01N 21/15* (2013.01); *G01N 21/0332* (2013.01)

(58) Field of Classification Search
  CPC ....................................................... G01N 21/15
  See application file for complete search history.

(56) References Cited

U.S. PATENT DOCUMENTS

| 3,621,757 | A | * | 11/1971 | Bottoms | .................. | F15B 11/10 |
| | | | | | | 91/382 |
| 4,330,206 | A | | 5/1982 | Gausmann et al. | | |
| 5,563,737 | A | | 10/1996 | Kamrat | | |
| 6,967,151 | B2 | | 11/2005 | Song et al. | | |
| 7,821,641 | B2 | | 10/2010 | Wagner et al. | | |
| 2002/0018200 | A1 | | 2/2002 | Salo | | |
| 2007/0052949 | A1 | | 3/2007 | Salo | | |
| 2007/0242720 | A1 | | 10/2007 | Eckles et al. | | |
| 2012/0070754 | A1 | * | 3/2012 | Smith | ............... | H01M 8/04104 |
| | | | | | | 429/428 |
| 2012/0085144 | A1 | * | 4/2012 | Krolak | ................... | G01N 21/15 |
| | | | | | | 73/19.1 |

FOREIGN PATENT DOCUMENTS

| WO | WO 98/20338 A1 | 5/1998 |
| WO | WO 2012/045325 A1 | 4/2012 |

OTHER PUBLICATIONS

Finnish Search Report mailed on Jan. 22, 2015 for Application No. 20145539.

* cited by examiner

*Primary Examiner* — Tarifur Chowdhury
*Assistant Examiner* — Omar Nixon
(74) *Attorney, Agent, or Firm* — Buchanan Ingersoll & Rooney PC

(57) ABSTRACT

A method and an arrangement are disclosed in connection with a measurement arrangement of optical parameters of a separate sample taken from a process liquid, in which method a sample is taken from the process liquid. The sample can be arranged into a sample vessel provided with at least one measurement window, and optical parameters of the sample in the sample vessel are measured through the measurement window. In the sample in the sample vessel, a flow is produced which can be used to mitigate (e.g., prevent) the measurement window surface in contact with the sample from getting dirty. A back-and-forth flow can be produced in the sample residing in the sample vessel by means of pressure variation focused on the sample, and the back-and-forth flow can be focused on the surface of the optical measurement window.

20 Claims, 3 Drawing Sheets

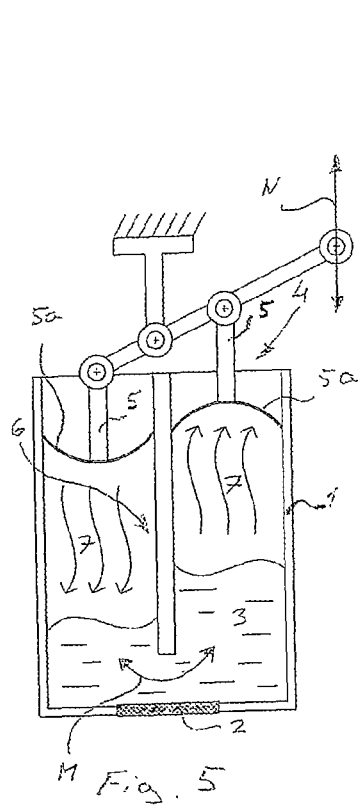
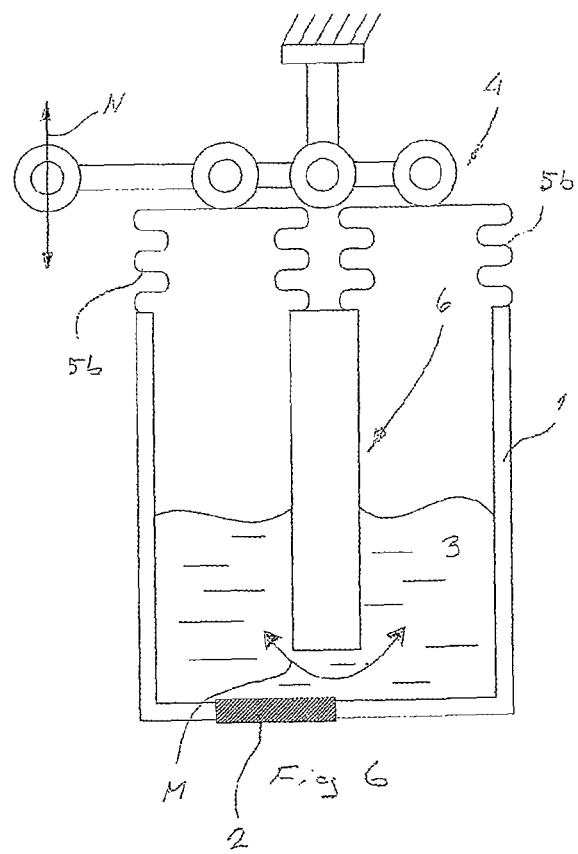
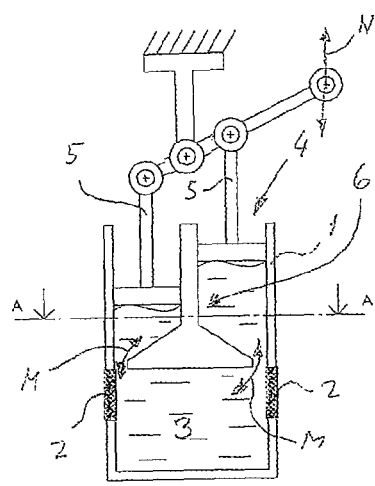
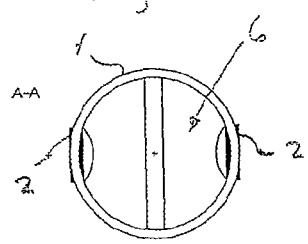
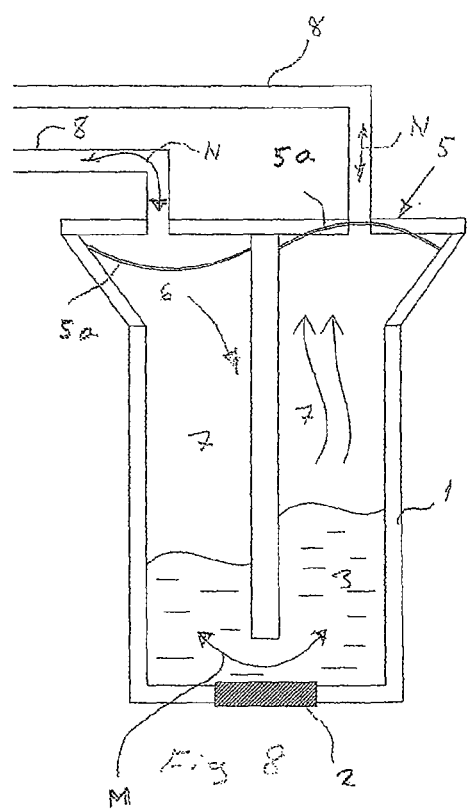

METHOD AND ARRANGEMENT IN CONNECTION WITH SEPARATE SAMPLE TAKEN FROM PROCESS LIQUID

RELATED APPLICATION(S)

This application claims priority under 35 USC §119 to Finnish Application No. 20145539 filed in Finland on Jun. 11, 2014. The entire content of which is hereby incorporated by reference in its entirety.

FIELD

The disclosure relates to a method in connection with a measurement arrangement of optical parameters of a separate sample taken from a process liquid.

BACKGROUND INFORMATION

When optical parameters of liquids are measured from separate samples, a drawback in measuring samples taken from process liquids of industrial processes, for example, is that foreign substances in the samples, or organic components often found in the mixture, tend to accumulate on the optical surfaces of optical windows, such as measuring prisms. This can take place, for example, when a sample solution is in a static, non-flowing state. As an example of measurements concerning optical parameters of solutions, measurements taken with a refractometer, for example, are described in the U.S. Pat. No. 6,967,151.

Sedimentation relating to measurements of solutions including solid matters can be an issue. A solid matter can find its way, as a result of gravity, towards the bottom of a measurement vessel, such as a sample vessel.

Concerning oil-based emulsions, for example, is the separation of oil into a different phase. This may also take place when measuring milk samples, for example, in which fat globules find their way to the surface of the liquid both on the walls of a sample vessel and the optical surfaces of the measurement window.

Due to surface potential characteristics, certain substances can possess the trend that, over time, their concentration increases right next to the surface. When sugar solutions or solutions of the wood-processing industry, for example, are measured, the measurement result has the tendency of increasing as a function of time.

Attempts to solve the aforementioned issues have been made by using mixers of various kinds in connection with a sample vessel. As mixers, either small, blade-type, whisk-type or magnet pill type mixers have been used, arrangements in which a magnet element is placed in the measurement vessel, which can be made to rotate by means of a magnetic field and to mix the liquid. Mechanical rotation or back-and-forth movement may be incorporated into the above arrangements.

For small capacities, typically approximately 5-10 ml, an adequate local rate of flow cannot be focused on optical measurement surfaces. If a mixer's rotation speed is increased, the result with whisk-type mixers, for example, is the mixing of air into the sample, which in turn leads to foaming. A mixer in a small sample cuvette cannot be installed eccentrically enough in relation to the measurement cuvette. The result is that even a very low rotation speed can create a vortex in the cuvette, and air can be mixed into the sample, or the sample can escape from the center of the cuvette to the edges. The optical measurement surface can be located at the bottom of the cuvette, so in a situation like this it is easily left without a sample.

Due to the issues described in the above, the known solutions do not allow a strong enough local flow rate to be achieved towards the optical surfaces of a sample vessel so as to remove the build-up effects the sample creates, or to maintain efficient mixing of the sample.

Many of the known measurement devices are also provided with thermostats to keep the temperature of the sample being measured constant. The previously known mixing arrangements do not shift the vertical layers of the sample efficiently enough, whereby the measurement result is not the best possible.

SUMMARY

A method is disclosed for measurement of optical parameters of a separate sample taken from a process liquid, the method comprising: taking a sample from the process liquid; arranging the sample into a sample vessel provided with at least one optical measurement window; measuring optical parameters of the sample in the sample vessel through the measurement window; producing a flow in the sample in the sample vessel, such a flow being selected to mitigate the measurement window surface which is in contact with the sample, from becoming dirty; generating a back-and-forth flow in the sample in the sample vessel by a pressure variation directed on the sample; and directing the back-and-forth flow on the surface of the optical measurement window.

An arrangement is disclosed for measuring optical parameters of a separate sample taken from a process liquid, the arrangement comprising: a sample vessel having at least one optical measurement window, the optical measurement window being configured and arranged to obtain a measurement of optical parameters of a sample once placed in the sample vessel through the optical measurement window; and means to produce a flow in the sample vessel to mitigate a measurement window surface which is in contact with the sample from becoming dirty, wherein the means to produce the flow in the sample includes at least one structure for producing a back-and-forth flow in the sample with a pressure variation, flow guiding structures for directing the back-and-forth flow to the surface of the optical window.

BRIEF DESCRIPTION OF THE DRAWINGS

The disclosure is explained below with reference to the exemplary embodiments shown in the drawings. In the drawings:

FIG. 5 is a schematic side view of an exemplary embodiment of the arrangement of the disclosure;

FIG. 6 is a schematic side view of an exemplary embodiment of the arrangement of the disclosure;

FIGS. 7A and 7B are schematic side views and cutaway views in the direction of arrows A-A of an exemplary embodiment of the arrangement of the disclosure;

FIG. 8 is a schematic side view of an exemplary embodiment of the arrangement of the disclosure.

DETAILED DESCRIPTION

In accordance with an exemplary embodiment, a method is disclosed in connection with a measurement arrangement of optical parameters of a separate sample taken from a process liquid, in which method a sample is taken from the process liquid, the sample is arranged into a sample vessel provided with at least one optical measurement window, and the optical parameters of the sample in the sample vessel are measured through the window, and in which method a flow is produced in the sample in the sample vessel, such a flow mitigating (e.g., preventing) the measurement window surface which is in contact with the sample from getting dirty (e.g., to a desired level where the measurement arrangement operation becomes inaccurate to a desired tolerance, or unusable).

In accordance with an exemplary embodiment, an arrangement is disclosed for measuring the optical parameters of a separate sample taken from a process liquid, which arrangement can include a sample vessel provided with at least one optical measurement window, arranged to receive the sample taken from the process liquid, whereby the optical measurement window is arranged to allow the measurement of the optical parameters of the sample in the sample vessel through the optical measurement window, and which arrangement can include means that are arranged to produce a flow in the sample, and which is arranged to prevent the measurement window surface which is in contact with the sample from getting dirty.

In accordance with an exemplary embodiment, the method according to the disclosure can include establishing a back-and-forth flow in a sample residing in a sample vessel by means of pressure variation directed at the sample, and in that the back-and-forth flow is focused on the surface of an optical measurement window. The arrangement according to the disclosure, can include that the means that are arranged to create the flow in the sample can include at least one structure creating the back-and-forth flow in the sample by means of pressure variation, and that the back-and-forth flow created in the sample by means of pressure variation is led to the surface of the optical measurement window by means of the structures that guide the flow.

In accordance with an exemplary embodiment, the method and arrangement due their relative simplicity which results in low introduction costs of the disclosure and good reliability. In addition, the method and arrangement can have good adaptability, such that the disclosure may be adapted for different purposes. In accordance with an exemplary embodiment, the disclosure can make use of back-and-forth flow of a liquid sample in a sample vessel. The back-and-forth flow may be achieved by any suitable way, for example, by an arrangement working mechanically, electrically, pneumatically, or hydraulically. The flow may be precisely focused on the desired optical surface or surfaces. The disclosure may be applied to one or more capacity-based solutions.

Figure 1:
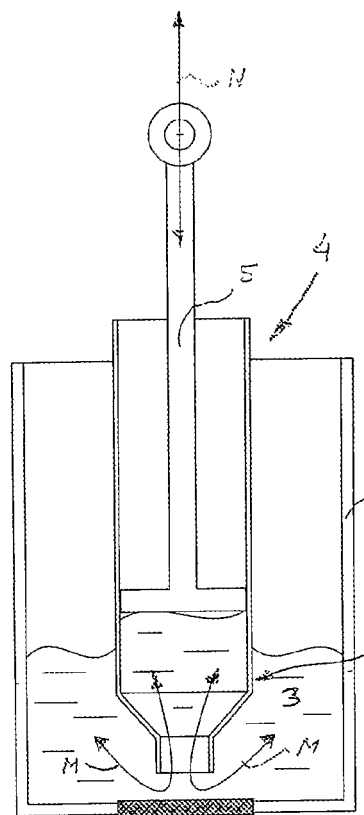
FIG. 1 is a schematic side view of an exemplary embodiment of the arrangement of the disclosure.

FIG. 1 is a schematic view of an exemplary embodiment of an arrangement of the disclosure. Reference number 1 denotes a sample vessel. Reference number 2 is used to denote an optical measurement window in the sample vessel. Reference number 3 refers to a sample in the sample vessel. The sample 3 can be a sample taken from a process liquid, such as an industrial process, in a suitable manner known to those skilled in the art.

The optical parameters of the sample 3 residing in the sample vessel 1 can be measured through its optical measurement window 2. For those skilled in the art, such measurements are known such that the measurements and technology need not be explained in greater detail herein. General reference made herein is to U.S. Pat. No. 6,067,151, which describes a measurement arrangement in which optical parameters of a liquid can be measured through an optical measurement window.

Measurements of this type can have the tendency, for the measurement window to become dirty. The dirty measurement window, for example, can cause errors in the measurement result. In known solutions, attempts have been made to clean the measurement window by creating a flow in the sample, which can help prevent the measurement window from getting dirty. However, known solutions have not achieved good results.

In accordance with an exemplary embodiment, the disclosure is based at least in part on utilizing the back-and-forth flow of a liquid sample in a sample vessel. The back-and-forth flow of the sample can be created by means which provide a pressure effect, for example, pressure variation, focused on the sample. The pressure variation and the consequential back-and-forth flow may be achieved by any suitable way, for example, by an arrangement working mechanically, electrically, pneumatically, or hydraulically.

In the arrangement according to FIG. 1, the pressure variation can be achieved by means 4 which can include a piston assembly (or piston) 5 and structures 6, with which the back-and-forth flow of the sample created by the back-and-forth moving piston means is led to the surface of the optical window. The movement of the piston means 5 is shown in FIG. 1 with the aid of arrow N and the back-and-forth flow correspondingly with the aid of arrows M. The structures 6, by means of which the flow is directed on the surface of the measurement window, may include nozzle structures and/or guiding wall structures.

In the embodiment according to FIG. 1, liquid is moved in the sample vessel 1 by means of one piston means. There may be more than one piston means, for example, two piston means can be used. The structure may be enclosed and entirely filled by the liquid being measured, whereby no evaporation or changes in the sample will take place. The sample vessel 1 can be temperature-controlled. In accordance with an exemplary embodiment, heat can be transferred to the sample moving back and forth, as this means that temperature gradients are thereby avoided. In accordance with an exemplary embodiment, a disposable injection syringe may act as the means 4 in the embodiment of FIG. 1, by means of which the desired back-and-forth flow may be established for the sample with suitable mechanical equipment. The use of more disposable injection syringes, for example, such as two of them can be used.

Figure 2:
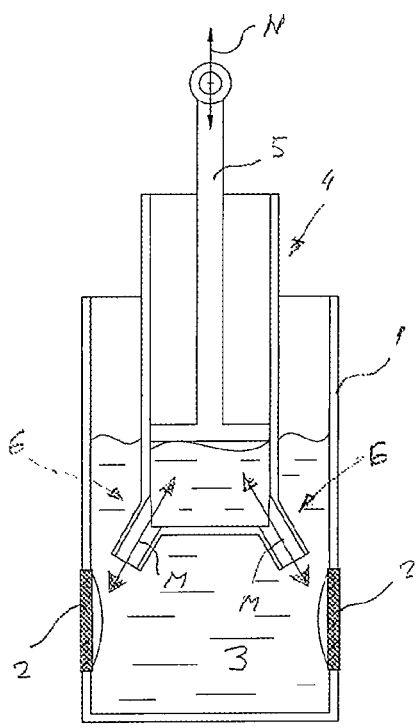
FIG. 2 is a schematic side view of an exemplary embodiment of the arrangement of the disclosure.

The means 4 may be formed entirely freely, according to the sample vessel 1 being used, for example. FIG. 2 shows an exemplary embodiment in which the sample vessel 1 has two optical measurement windows 2. The means 4 with which the pressure effect is created, and the structures 6, for example, the nozzle structures can be so formed that the flow can be focused on both measurement windows. In FIG. 2, the same reference numerals and marks as in FIG. 1 are used at corresponding points.

Figure 3:
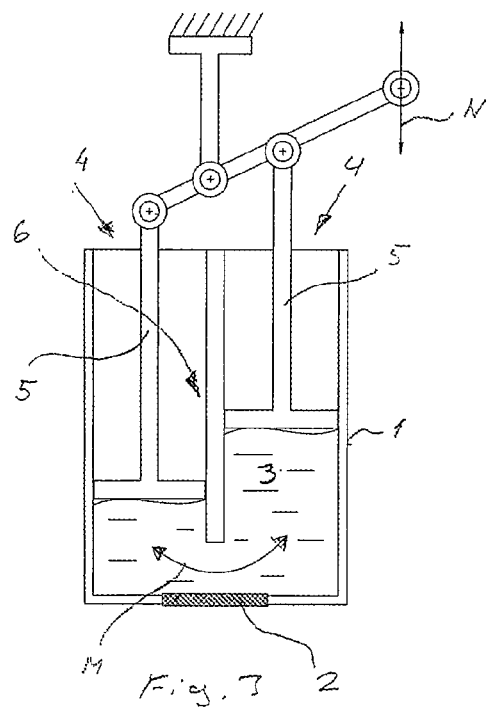
FIG. 3 is a schematic side view of an exemplary embodiment of the arrangement of the disclosure.

FIG. 3 shows a double-action embodiment. This embodiment uses means 4 with two piston means 5. The piston means 5 can be used in a synchronized manner by means of a suitable mechanism so that they move simultaneously in opposite directions. The structures 6, by means of which the flow can be guided on the measurement window 2, includes a separating wall the design of which directs the liquid flow on the optical measurement window 2. In FIG. 3, the same reference numerals and marks as in FIGS. 1 and 2 are used at corresponding points.

Figure 4:
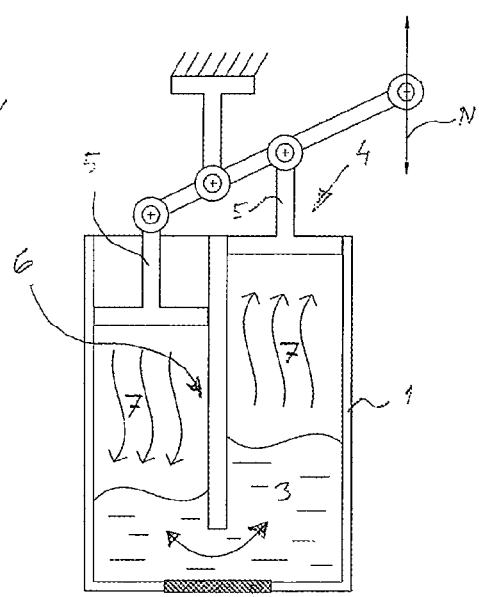
FIG. 4 is a schematic side view of an exemplary embodiment of the arrangement of the disclosure.

In the embodiment according to FIGS. 1-3, the piston means 5 can directly affect the sample liquid 3. This, however, is not the only option but the piston means may also affect the sample indirectly. In accordance with an exemplary embodiment, the term indirectly here can mean that the piston means may affect the sample in the sample vessel through air or gas in the sample vessel. An application of this kind is shown in FIG. 4. In FIG. 4, the same reference numerals and marks as in FIGS. 1-3 are used at corresponding points. In FIG. 4, the air or gas acting as the transmitter substance is denoted by number 7. In other respects, the embodiment of FIG. 4 essentially corresponds to that of FIG. 3.

The piston means 5 used in the disclosure may also be implemented in various ways. FIGS. 1-4 show applications where the piston means can be implemented with a known piston mechanism. FIG. 5 shows an embodiment where the piston means 5 can be implemented with diaphragms 5a. In the exemplary embodiment of FIG. 5, the diaphragms can be affected mechanically. In FIG. 5, the same reference numerals and marks as in FIGS. 1-4 are used at corresponding points. With the exception of the piston means, the embodiment of FIG. 5 essentially corresponds to that of FIG. 4.

FIG. 6 shows an exemplary embodiment according to the disclosure, in which the means 4, which establish the pressure variation, which in turn creates the back-and-forth flow in the sample 3, can be formed with the aid of bellows means 5b. In FIG. 6, the same reference numerals and marks as in FIGS. 1-5 are used at corresponding points.

FIGS. 7A and 7B show an exemplary embodiment of the disclosure, in which the back-and-forth flow generated with the piston means 5 can be led to two measurement windows 2 by means of structures 6 including a separating wall shaped in a special manner. In FIGS. 7A and 7B, the same reference numerals and marks as in FIGS. 1-6 are used at corresponding points.

The piston means implemented with diaphragms 5a may also be affected by means of external pressure sources of various kind, for example, by leading the pressure effect alternately on both piston means. FIG. 8 shows such an embodiment. In the embodiment of FIG. 8, the piston means 5 formed with diaphragms 5b can be affected by means of the pressure effect that is led through channels 8. The pressure effect may be generated by means of air or gas. In FIG. 8, the same reference numerals and marks as in the preceding figures are used at corresponding points.

Figure 9:
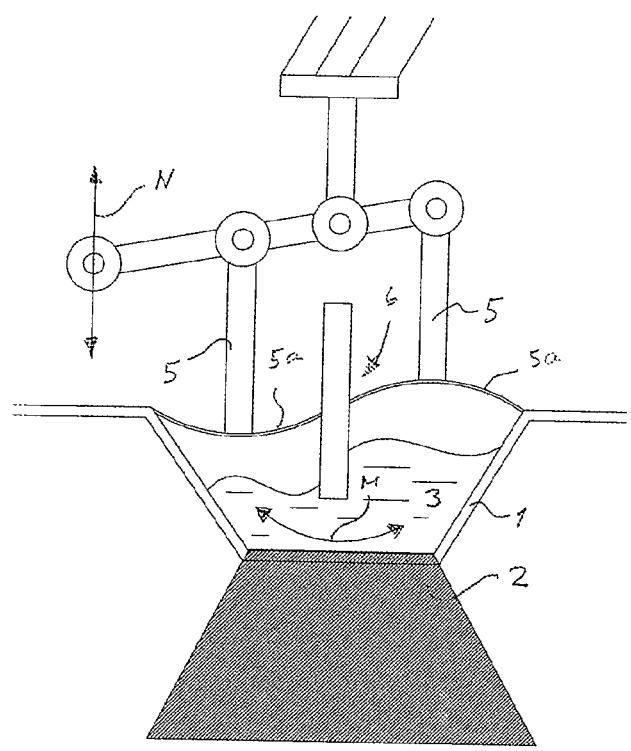
FIG. 9 is a schematic side view of an exemplary embodiment of the arrangement of the disclosure.

The disclosure is also applicable to laboratory refractometers in which a sample taken from a process is placed in a normally conical recess acting as the sample vessel. At the bottom of the recess there is a measurement window, such as a measuring prism. FIG. 9 shows such an application in principle. In FIG. 9, the same reference numerals and marks as in FIGS. 1-8 are used at corresponding points.

In the application of FIG. 9, the piston means can be mechanically affected, and by means of the structure 6 formed by the separating wall, the back-and-forth liquid flow generated by the piston means can be effectively directed in the direction of the measurement window 2 surface at the bottom of the sample vessel 1 onto the surface in question. Such an arrangement can produce a reliable and stable measurement result. In the structure 6, constant-temperature liquid circulation or another arrangement producing a constant temperature can be additionally added.

In accordance with an exemplary embodiment, a fast flowing pulse is focused on the optical window or windows of the measurement vessel, which can produce fast cleaning of the optical window, good mixing of the sample, and even temperature of the sample. The flowing rate of the sample may locally be of the shape of a sine wave. In an application using one piston means, for example, the top speed of the flow can be achieved at the ejection phase of the piston in the shape of an asymmetric graph. The parts that are in contact with the sample may be either parts that are easy to clean or also disposable parts.

This disclosure sets forth examples as shown in the figures. The disclosure is, however, not restricted to the examples of the figures in any way, but the disclosure may be varied entirely freely within the scope of the claims.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A method for measurement of optical parameters of a separate sample taken from a process liquid, the method comprising:
   taking a sample from the process liquid;
   arranging the sample into a sample vessel provided with at least one optical measurement window;
   measuring optical parameters of the sample in the sample vessel through the at least one optical measurement window;
   producing a flow in the sample in the sample vessel, such a flow configured to mitigate the surface of the at least one optical measurement window which is in contact with the sample, from becoming dirty;
   generating a back-and-forth flow comprising a fast flowing pulse in the sample in the sample vessel by a pressure variation directed on the sample; and
   directing the back-and-forth flow on the surface of the at least one optical measurement window wherein an angle of the flow directed on the surface of the at least one optical measurement window is divergent from an angle parallel to the surface of the at least one optical measurement window.

2. The method as claimed in claim 1, comprising:
   producing the pressure variation by one or more pistons moving back and forth.

3. The method as claimed in claim 1, comprising:
   producing the pressure variation by a diaphragm.

4. The method as claimed in claim 1, comprising:
   producing the pressure variation by a bellows.

5. The method as claimed in claim 1, comprising:
   directing the back-and-forth flow produced in the sample to the surface of the optical window by flow guide structures.

6. The method as claimed in claim 5, wherein the structures guiding the flow comprise:
   a guiding wall structure.

7. The method as claimed in claim 5, wherein the structures guiding the flow comprise:
   a nozzle structure.

8. The method as claimed in claim 1, comprising:
producing the pressure variation by two pistons, which move simultaneously in opposite directions.

9. The method as claimed in claim 1, comprising:
controlling a temperature of the sample vessel to produce a constant temperature of the sample.

10. The method as claimed in claim 1, comprising:
transferring heat to the sample moving back and forth to avoid temperature gradients in the sample.

11. An arrangement for measuring optical parameters of a separate sample taken from a process liquid, the arrangement comprising:
a sample vessel having at least one optical measurement window, the at least one optical measurement window being configured and arranged to obtain a measurement of optical parameters of a sample once placed in the sample vessel through the at least one optical measurement window; and
means for producing a flow in the sample vessel to mitigate a surface of the at least one optical measurement window which is in contact with the sample from becoming dirty, wherein the means for producing the flow in the sample includes at least one structure for producing a back-and-forth flow comprising a fast flowing pulse in the sample with a pressure variation, flow guiding structures for directing the back-and-forth flow to the surface of the at least one optical measurement window wherein an angle of the flow directed on the surface of the at least one optical measurement window is divergent from an angle parallel to the surface of the at least one optical measurement window.

12. The arrangement as claimed in claim 11, wherein the means for producing the back-and-forth flow in the sample by a pressure variation comprises:
a piston.

13. The arrangement as claimed in claim 11, wherein the means for producing the back-and-forth flow in the sample by a pressure variation comprises:
a diaphragm.

14. The arrangement as claimed in claim 11, wherein the means for producing the back-and-forth flow in the sample by pressure variation comprises:
a bellows.

15. The arrangement as claimed in claim 11, wherein the structures guiding the flow comprise:
a guiding wall structure.

16. The arrangement as claimed in claim 11, wherein the structures guiding the flow comprise:
a nozzle structure.

17. The arrangement as claimed in claim 11, wherein the means for producing the back-and-forth flow in the sample by a pressure variation comprises:
two pistons which move simultaneously in opposite directions.

18. The arrangement as claimed in claim 11, comprising
a temperature control for controlling a temperature of the sample vessel to produce a constant temperature of the sample.

19. The arrangement as claimed in claim 11, comprising:
a heater for transferring heat to a sample when moving back and forth to avoid temperature gradients in the sample.

20. The arrangement as claimed in claim 11, wherein the at least one optical measurement window comprises:
two optical measurement windows.

* * * * *